United States Patent
Tseng et al.

(10) Patent No.: US 10,210,625 B2
(45) Date of Patent: Feb. 19, 2019

(54) MEASUREMENT SYSTEM COMPRISING ANGLE ADJUSTMENT MODULE

(71) Applicant: Industrial Technology Research Institute, Hsinchu (TW)

(72) Inventors: Kun-Lung Tseng, New Taipei (TW); Ming-Hui Lin, Hsinchu County (TW); Shih-Wen Yang, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 234 days.

(21) Appl. No.: 14/927,488

(22) Filed: Oct. 30, 2015

(65) Prior Publication Data

US 2017/0124724 A1 May 4, 2017

(51) Int. Cl.
*H04N 7/18* (2006.01)
*G06T 7/60* (2017.01)
(Continued)

(52) U.S. Cl.
CPC ............... *G06T 7/60* (2013.01); *G01B 11/02* (2013.01); *G01B 11/24* (2013.01); *G06T 7/0004* (2013.01);
(Continued)

(58) Field of Classification Search
CPC ....................................................... G06T 7/60
(Continued)

(56) References Cited

U.S. PATENT DOCUMENTS

| 4,752,964 A * | 6/1988 | Okada ................ G05B 19/4207 |
| | | 356/608 |
| 5,048,965 A * | 9/1991 | Amir .................. G01N 21/8806 |
| | | 356/604 |

(Continued)

FOREIGN PATENT DOCUMENTS

| CN | 2835997 | 11/2006 |
| CN | 101419705 | 4/2009 |

(Continued)

OTHER PUBLICATIONS

Nebot etal., "Initial calibration and alignment of Low cost Inertial Navigation Units for land vehicle applications", Journal of Robotics Systems, Feb. 1999, pp. 81-92.

(Continued)

*Primary Examiner* — Leron Beck
(74) *Attorney, Agent, or Firm* — JCIPRNET (57) ABSTRACT

A measurement system comprises an illumination module, an image pickup device, an angle adjustment module, and a control unit. The illumination module is configured to illuminate an object. The image pickup device is configured to pick up an image of the object. The angle adjustment module is configured to adjust an relative angle between the object and the image pickup device. The control unit is electrically connected to the image pickup device and the angle adjustment module and configured to receive an image signal from the image pickup device. The control unit is configured to command the angle adjustment module to adjust the relative angle to at least three values. The image pickup device is (Continued)

configured to pick up images of the object respectively corresponding to the at least three values. The control unit is configured to calculate the relative angle between the object and the image pickup device.

13 Claims, 6 Drawing Sheets

(51) Int. Cl.
*G01B 11/02* (2006.01)
*G06T 7/00* (2017.01)
*G01B 11/24* (2006.01)

(52) U.S. Cl.
CPC ............... *G06T 2207/10152* (2013.01); *G06T 2207/30164* (2013.01)

(58) Field of Classification Search
USPC ........................................................ 348/142
See application file for complete search history.

(56) References Cited

U.S. PATENT DOCUMENTS

| | | | | |
|---|---|---|---|---|
| 5,581,347 A * | 12/1996 | Le Saux | ............... | G01M 11/025 356/124 |
| 5,923,020 A * | 7/1999 | Kurokawa | ......... | G01N 21/8806 235/454 |
| 6,011,620 A * | 1/2000 | Sites | .................... | G01N 21/896 356/239.1 |
| 6,535,250 B1 * | 3/2003 | Okisu | ....................... | G02B 7/08 250/334 |
| 6,795,200 B1 * | 9/2004 | Barman | ................ | G01B 11/022 356/606 |
| 7,107,168 B2 | 9/2006 | Oystol et al. | | |
| 7,478,552 B2 | 1/2009 | Gotthard et al. | | |
| 7,499,180 B2 | 3/2009 | Hattori | | |
| 8,159,653 B2 | 4/2012 | Shindo | | |
| 8,353,628 B1 * | 1/2013 | Yun | ........................ | H01J 37/244 378/207 |
| 8,411,270 B2 | 4/2013 | Zangooie et al. | | |
| 8,813,430 B2 | 8/2014 | Rees et al. | | |
| 9,032,832 B2 | 5/2015 | Wu | | |
| 9,661,310 B2 * | 5/2017 | Deng | ................. | H04N 13/0271 |
| 2002/0135776 A1 * | 9/2002 | Nishi | ................... | G03F 7/70775 356/500 |
| 2003/0007159 A1 * | 1/2003 | Franke | .................... | G01B 11/25 356/604 |
| 2004/0008773 A1 * | 1/2004 | Itokawa | ................ | G01S 3/7864 375/240.08 |
| 2004/0147121 A1 * | 7/2004 | Nakagaki | ............ | G03F 7/70683 438/689 |
| 2005/0237423 A1 * | 10/2005 | Nilson | ................. | A61B 5/0059 348/370 |
| 2006/0049480 A1 * | 3/2006 | Naka | .................... | G01N 21/211 257/521 |
| 2007/0091324 A1 * | 4/2007 | Paul | ...................... | G02B 21/365 356/623 |
| 2007/0216784 A1 * | 9/2007 | Yuyama | ............. | H04N 5/23293 348/239 |
| 2008/0153315 A1 * | 6/2008 | Morikazu | ......... | H01L 21/76898 438/795 |
| 2008/0273211 A1 * | 11/2008 | Schmitt | ................ | G01B 11/245 356/611 |
| 2009/0015823 A1 * | 1/2009 | Yoshikawa | ........ | G01N 21/4738 356/237.2 |
| 2009/0167867 A1 * | 7/2009 | Lin | ........................ | H04N 5/232 348/169 |
| 2009/0180108 A1 | 7/2009 | Bottini et al. | | |
| 2010/0328653 A1 * | 12/2010 | Liu | .................... | H04N 13/0425 356/218 |
| 2011/0023578 A1 * | 2/2011 | Grasser | .................. | G01C 15/00 73/1.75 |
| 2011/0083497 A1 * | 4/2011 | Matsumiya | ............ | G01B 5/008 73/105 |
| 2014/0172153 A1 * | 6/2014 | Nishibashi | ......... | G05B 19/4103 700/192 |
| 2014/0291511 A1 * | 10/2014 | Man | .................... | H01J 37/3002 250/307 |
| 2016/0086769 A1 * | 3/2016 | Kim | .................... | H01J 37/3005 250/310 |

FOREIGN PATENT DOCUMENTS

| | | |
|---|---|---|
| CN | 102042813 | 5/2011 |
| CN | 202471611 | 10/2012 |
| CN | 103473771 | 12/2013 |
| TW | 492540 | 6/2002 |

OTHER PUBLICATIONS

Fan etal., "A 6-degree-of-freedom measurement system for the accuracy of X-Y stages", Precision Engineering, Jan. 2000, pp. 15-23.
Williams etal., "Automated Positioning and Alignment Systems", Society of Automotive Engineers, Sep. 2000 , pp. 1-9.
Gao etal., "Measurement of multi-degree-of-freedom error motions of a precision linear air-bearing stage", Precision Engineering Jan. 2006, pp. 96-103.
"Office Action of China Counterpart Application", dated Sep. 25, 2018, p. 1-p. 7.

* cited by examiner

MEASUREMENT SYSTEM COMPRISING ANGLE ADJUSTMENT MODULE

TECHNICAL FIELD

The technical field relates to a measurement system.

BACKGROUND

Generally speaking, in the environment of workpiece production, the production speed of machinery is far greater than the speed of measuring the workpiece by a worker. The worker usually increases the measurement speed, which is, however, easy to cause that the measured value is not correct. An automatic measurement system may prevent the measure errors due to the worker. Nevertheless, when the workpiece is automatically produced, production errors may adversely affect the measurement result by the automatic measurement system. When the workpiece is measured by the worker, the worker may manually adjust the workpiece to prevent the production errors to affect the measurement of the unprocessed region. As a result, how to prevent the production errors from affecting the result of the automatic measurement is a main subject to research.

SUMMARY

One of exemplary embodiments provides a measurement system configured to measure an object. The measurement system comprises an illumination module, an image pickup device, an angle adjustment module, and a control unit. The illumination module is configured to illuminate the object. The image pickup device is configured to pick up an image of the object. The angle adjustment module is configured to adjust an relative angle between the object and the image pickup device. The control unit is electrically connected to the image pickup device and the angle adjustment module and configured to receive an image signal from the image pickup device. The control unit is configured to command the angle adjustment module to adjust the relative angle to at least three values. The image pickup device is configured to pick up images of the object respectively corresponding to the at least three values. The control unit is configured to calculate the relative angle between the object and the image pickup device according to the images of the object respectively corresponding to the at least three values and command the angle adjustment module to adjust the relative angle to a measurement angle according to the calculated relative angle, so as to pick up and measure the image of the object under the measurement angle.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
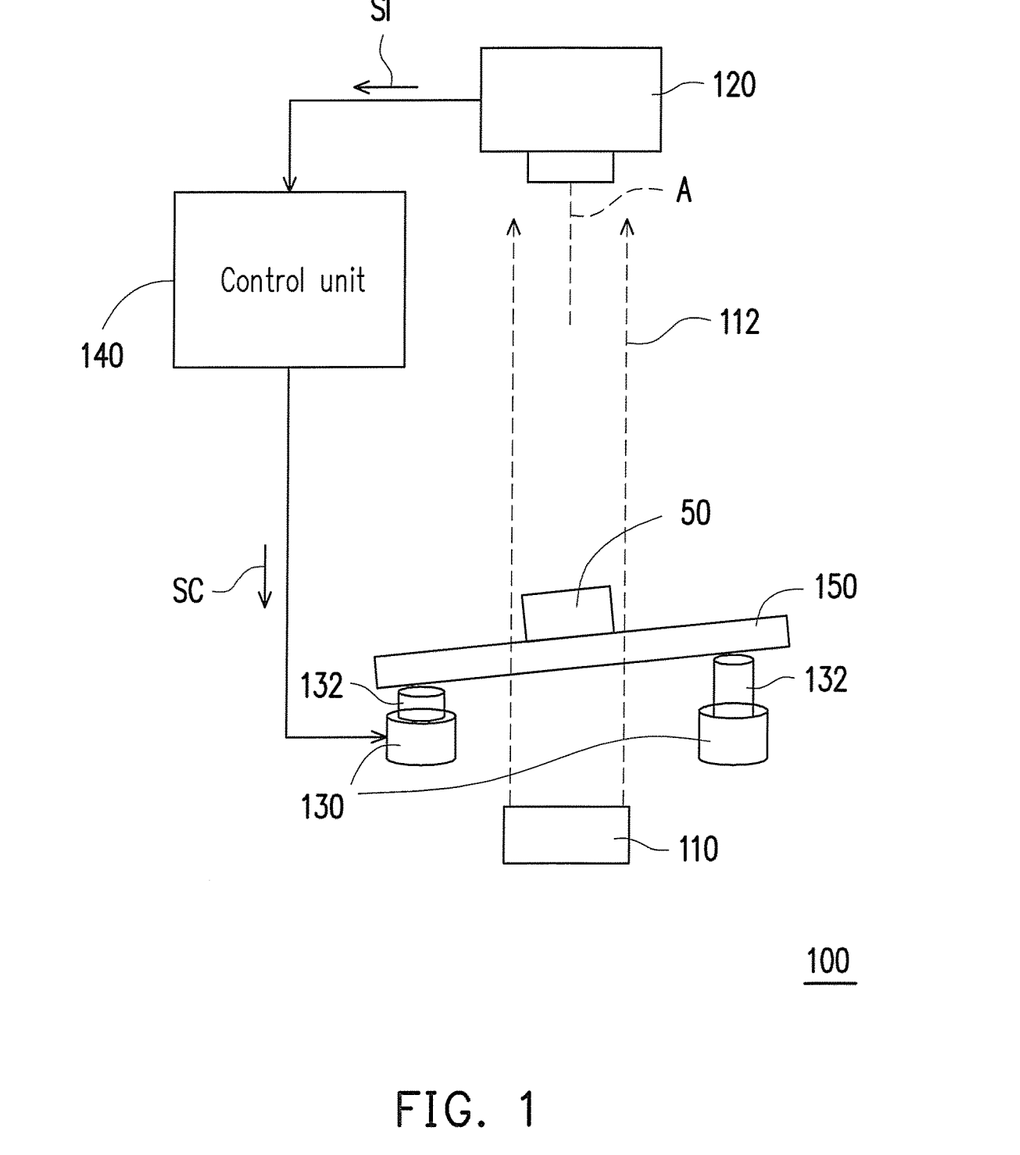
FIG. 1 is a schematic view of a measurement system according to an exemplary embodiment.
Figure 2:
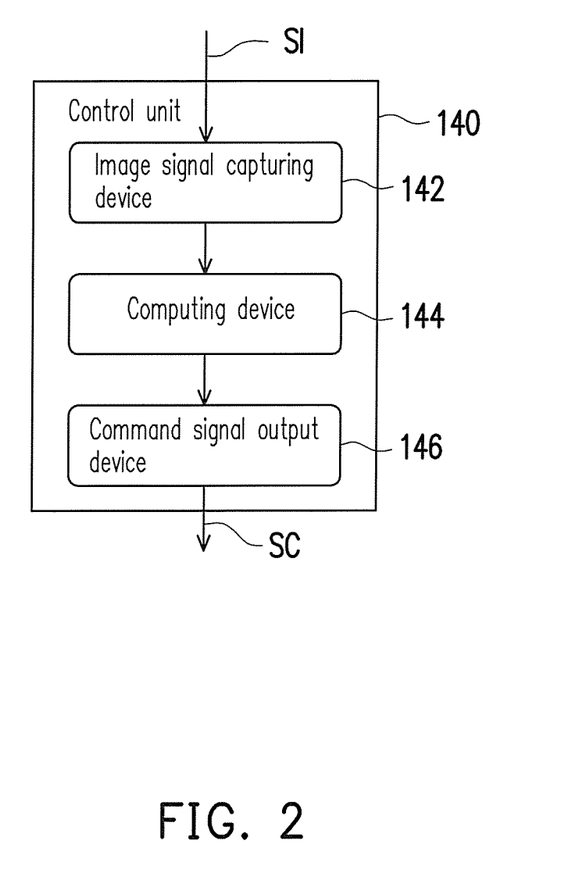
FIG. 2 is a block diagram of the control unit in FIG. 1.
Figure 3A:
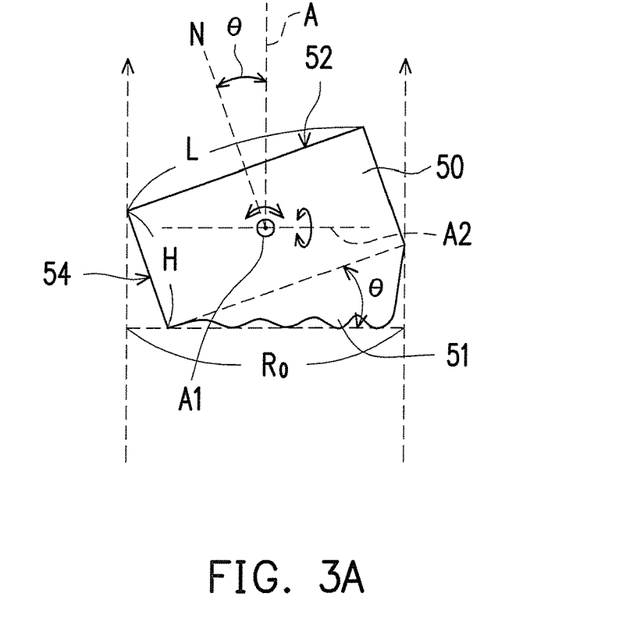
FIG. 3A shows the measurement parameters of the object in FIG. 1.
Figure 4:
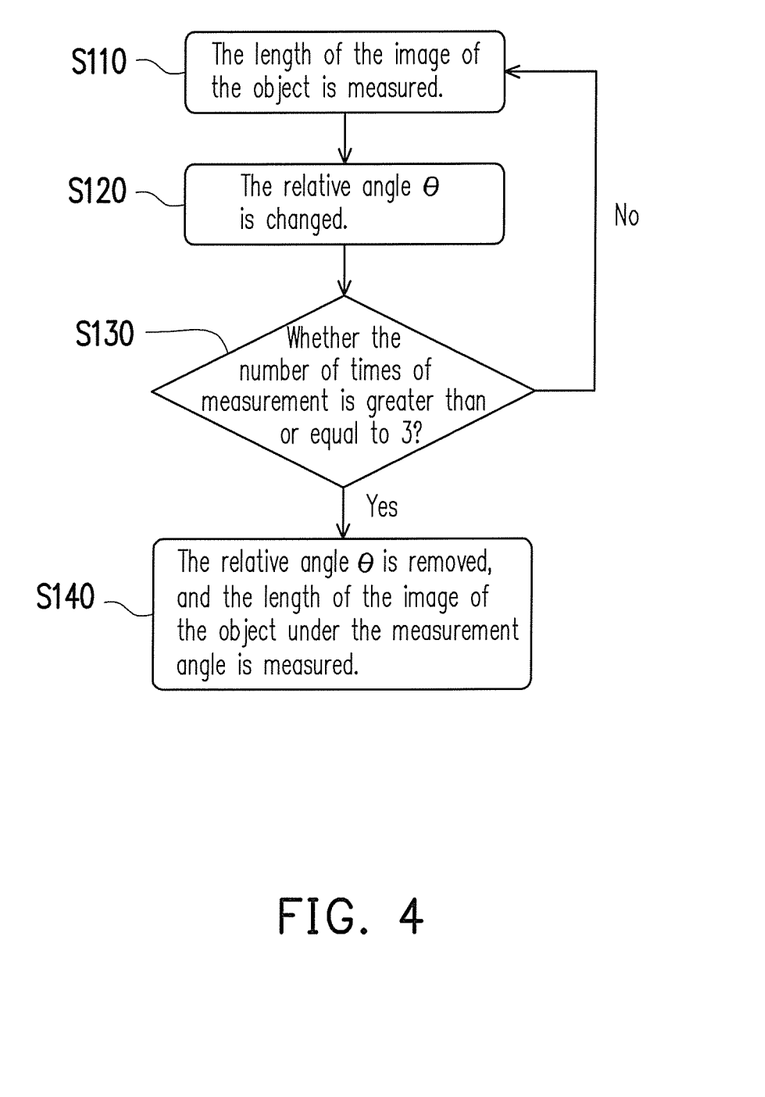
FIG. 4 shows the algorithm performed in the control unit in FIG. 1.

FIG. 1 is a schematic view of a measurement system according to an exemplary embodiment, FIG. 2 is a block diagram of the control unit in FIG. 1, FIG. 3A shows the measurement parameters of the object in FIG. 1, and FIG. 4 shows the algorithm performed in the control unit in FIG. 1. Referring to FIGS. 1 to 4, the measurement system 100 in this embodiment is configured to measure an object 50. The object 50 may be a processed or unprocessed workpiece. The measurement system 100 in this embodiment comprises an illumination module 110, an image pickup device 120, an angle adjustment module 130, and a control unit 140.

The illumination module 110 is configured to illuminate the object 50. In this embodiment, the illumination module 110 is configured to provide a plane light source emitting a light 112 to the object 50, wherein the light 112 may be a parallel light or a diffusive light.

The image pickup device 120 is configured to pick up an image of the object 50. In this embodiment, the image pickup device 120 may be a camera comprising a charge coupled device (CCD) or a complementary metal oxide semiconductor (CMOS) image sensor having any appropriate resolution such as 5K, 4K, or Full HD.

The angle adjustment module 130 is configured to adjust an relative angle $\theta$ between the object 50 and the image pickup device 120. In this embodiment, the angle adjustment module 130 comprises at least one actuator 132 (a plurality of actuator 132 are exemplarily shown in FIG. 1) supporting back-and-forth motion. The angle adjustment module 130 may comprise a motion controller (not shown) and at least one actuator 132. The motion controller may control the motion of the actuator 132. The actuator 132 may comprise at least one of a motor, an oil hydraulic press, and gears.

The control unit 140 is electrically connected to the image pickup device 120 and the angle adjustment module 130 and configured to receive an image signal SI from the image pickup device 120. The control unit 140 is configured to command the angle adjustment module 130 to adjust the relative angle $\theta$ to at least three values. The image pickup device 120 is configured to pick up images of the object 50 respectively corresponding to the at least three values. The control unit 140 is configured to calculate the relative angle $\theta$ between the object 50 and the image pickup device 120 according to the images of the object 50 respectively corresponding to the at least three values and command the angle adjustment module 130 to adjust the relative angle $\theta$ to a measurement angle according to the calculated relative angle $\theta$, so as to pick up and measure the image of the object 50 under the measurement angle. In this embodiment, the control unit 140 may be a computer or a field programmable gate array (FPGA).

Specifically, referring to FIG. 3A, in this embodiment, the relative angle $\theta$ may be defined as the included angle between the normal of a measured surface 52 and the optical axis A of the image pickup device 120. In FIG. 3A, L is the length of the measured surface 52, H is the height of a processed surface 54 of the object 50. In this embodiment, the object 50 is disposed between the illumination module 110 and the image pickup device 120. As a result, the image pickup device 120 may pick up the shadow of the object 50. In FIG. 3A, $R_0$ is the length of the shadow. $R_0$ may be measured by the control unit 140, but $R_0$ is not the length of the measured surface 52 since the relative angle $\theta$ is not zero. If $R_0$ is deemed the length of the measured surface 52, the measured length of the measured surface 52 has an error.

Moreover, L, H, $\theta$, and $R_0$ satisfy the following geometric relationship:

$$L \cdot \cos\theta + H \cdot \sin\theta = R_0 \quad \text{Equation (1)}$$

Then, the control unit 140 may command the angle adjustment module 130 to rotate the object 50 by $\theta1$, so that the relative angle becomes $\theta+\theta1$, and $R_1$ is the length, measured by the control unit 140, of the shadow of the object 50 picked up by the image pickup device 120 when the relative angle is $\theta+\theta1$. As a result, the following geometric relationship may be obtained:

$$L \cdot \cos(\theta+\theta1) + H \cdot \sin(\theta+\theta1) = R_1 \quad \text{Equation (2)}$$

After that, the control unit 140 may command the angle adjustment module 130 to rotate the object 50 by $\theta2$, so that the relative angle becomes $\theta+\theta2$, and $R_2$ is the length, measured by the control unit 140, of the shadow of the object 50 picked up by the image pickup device 120 when the relative angle is $\theta+\theta2$. As a result, the following geometric relationship may be obtained:

$$L \cdot \cos(\theta+\theta2) + H \cdot \sin(\theta+\theta2) = R_2 \quad \text{Equation (3)}$$

In Equations (1), (2), and (3), L, H, and $\theta$ are unknown, and $\theta1$, $\theta2$, $R_0$, $R_1$, and $R_2$ are known. Since three equations can solve three unknowns, $\theta$ may be calculated by the control unit 140.

After the value of $\theta$ is obtained, the control unit 140 may command the angle adjustment module 130 to adjust the relative angle $\theta$ to a measurement angle, for example, 0 degree. In this embodiment, under the measurement angle, i.e. 0 degree, the optical axis A of the image pickup device 120 is substantially perpendicular to the measured surface 52 of the object 50. Then, the image pickup device 120 may pick up the image of the object 50 under the measurement angle, and the control unit 140 may measure the length of the image of the object 50. At this time, since the optical axis A of the image pickup device 120 is substantially perpendicular to the measured surface 52 of the object 50, the measured length of the image of the object 50 is L. That is to say, the measurement system 100 may accurately measure the length of the measured surface 52 of the object 50 without affected by an production error or irregular structure 51 of the object 50. Therefore, the measurement system 100 may achieve accurate and stable automatic measurement, which facilitates mass production and increases the application of automatic detection. Moreover, the measurement system 100 may be included in the quality control system to prevent the measurement errors and long operation time due to people.

Figure 3B:
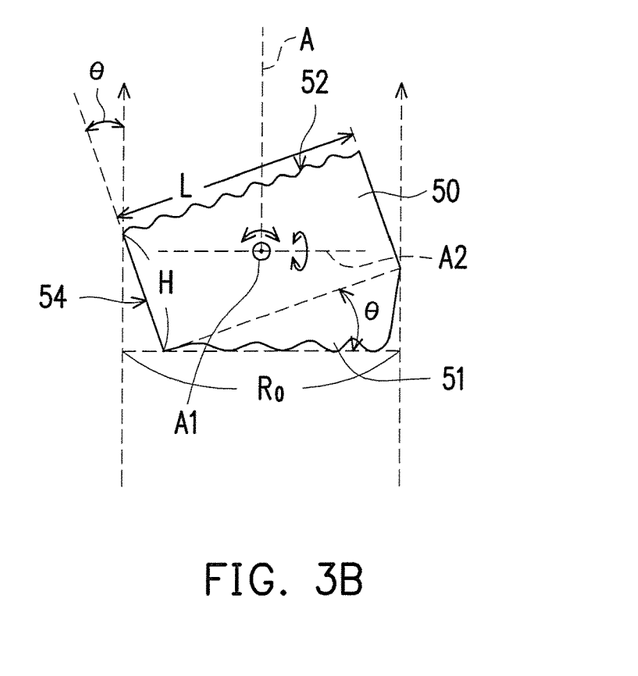
FIG. 3B shows the measurement parameters of the object in FIG. 1 in another embodiment.

In another embodiment, as shown in FIG. 3B, the relative angle $\theta$ may be defined as the included angle between the processed surface 54 of the object 50 and the optical axis A of the image pickup device 120. As a result, under the measurement angle, for example, 0 degree, the optical axis A of the image pickup device 120 is substantially parallel to the processed surface 54 of the object 50. In this embodiment, the measured surface 52 may be irregular as shown in FIG. 3B. The aforementioned equations (1), (2) and (3) and the aforementioned solution for the equations (1), (2), and (3) may also be suitable for the definition of the relative angle $\theta$ in this embodiment (i.e. the relative angle $\theta$ is defined as the included angle between the processed surface 54 of the object 50 and the optical axis A of the image pickup device 120); that is, the aforementioned equations (1), (2), and (3) and the solution therefor may also be applied to this embodiment (i.e. the embodiment of FIG. 3B).

In this embodiment, as shown in FIG. 2, the control unit 140 comprises an image signal capturing device 142, a computing device 144, and a command signal output device 146. The image signal capturing device 142 is configured to receive the image signal SI from the image pickup device 120. The resolution of the image signal SI may be 5K, 4K, Full HD, or any other appropriate resolution. The computing device 144 is configured to perform an algorithm to calculate the relative angle $\theta$. The command signal output device 146 is configured to output a command signal SC to the angle adjustment module 130 so as to adjust the angle adjustment module 130 according to the calculated relative angle. In this embodiment, the command signal SC may command the angle adjustment module 130 to adjust the relative angle to the measurement angle, so as to pick up and measure the image of the object 50 under the measurement angle.

Specifically, the algorithm performed by the computing device 144 may comprise the steps S110, S120, S130, and S140 shown in FIG. 4. First, in the step S110, the length of the image of the object 50 (e.g. the length of the shadow $R_0$ of the object 50) is measured. The orientation and range of the length of the image to be measured may be determined by an operator. In this step, $R_0$, $R_1$, or $R_2$ may be measured and obtained. Then, in the step S120, the relative angle $\theta$ is changed. For example, the relative angle $\theta$ is changed to $\theta+\theta1$ or $\theta+\theta2$. After that, in the step S130, whether the number of times of measurement is greater than or equal to 3 is determined. If no, the step S110 is performed. If yes, the step S140 is performed. In the step S140, the relative angle $\theta$ is removed, and the length of the image of the object 50 under the measurement angle is measured.

In this embodiment, the relative angle is an angle rotating around a single axis A1. However, in other embodiments, the relative angle may comprise two angle component respectively rotating around two different axes A1 and A2, and the command signal SC may command the angle adjustment module 130 to rotate around at least one of the axis A1 and the axis A2. In this embodiment, the axis A1 may be perpendicular to the axis A2. When the object 50 is rotated around two axes A1 and A2, the relative angle $\theta$ may be changed to three different values or more than three different values, and each of the values may comprises two angle component respectively around the axes A1 and A2. The length of the image of the object 50 may be measured three times or more than three times under the three or more different values, so as to obtain three or more different equations like Equations (1)-(3). The number of the equations may be determined based on the number being enough to solve the unknowns.

In this embodiment, the measurement system 100 further comprises a carrier 150 configured to carrying the object 50, wherein the angle adjustment module 130 is connected to the carrier 150 and configured to rotate the carrier 150 so as to rotate the object 50. The carrier 150 may be a stage or a jig to support the object 50. Clips may be set on the stage to fix the object 50 on the stage.

Figure 5:
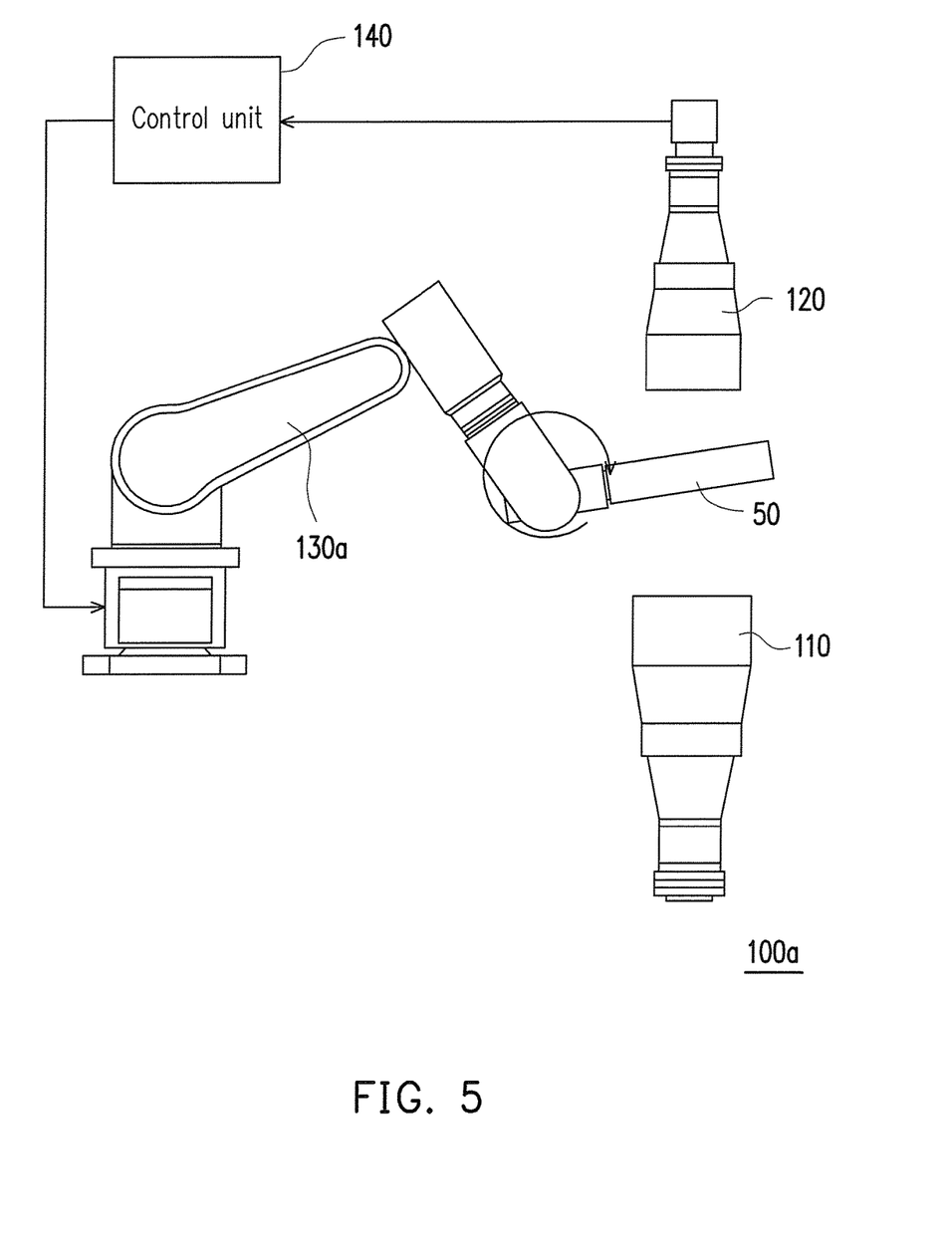
FIG. 5 is a schematic view of a measurement system according to another exemplary embodiment.

FIG. 5 is a schematic view of a measurement system according to another exemplary embodiment. Referring to FIG. 5, the measurement system 100*a* in this embodiment is similar to the measurement system 100 in FIG. 1, and the main difference therebetween is as follows. In this embodiment, the angle adjustment module 130a is a manipulator configured to fix the object 50 and adjust an orientation of the object 50. As a result, the relative angle between the object 50 and the image pickup device 120 may be adjusted by the manipulator.

Figure 6:
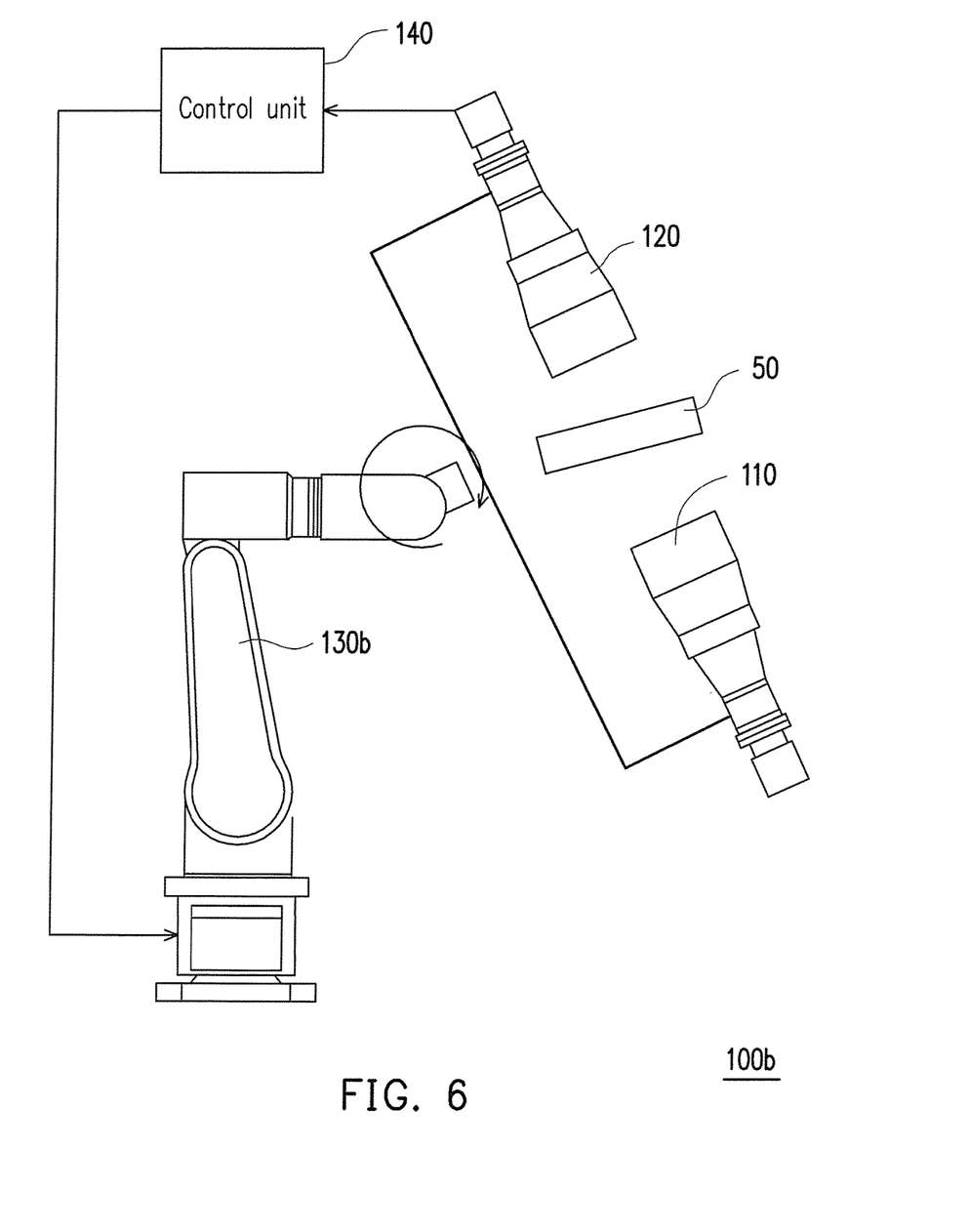
FIG. 6 is a schematic view of a measurement system according to another exemplary embodiment.

FIG. 6 is a schematic view of a measurement system according to another exemplary embodiment. Referring to FIG. 6, the measurement system 100b in this embodiment is similar to the measurement system 100 in FIG. 1, and the main difference therebetween is as follows. In this embodiment, the angle adjustment module 130b is a manipulator configured to fix the image pickup device 120 and the illumination module 110 and adjust an orientation of the image pickup device 120 and the illumination module 110. As a result, the relative angle between the object 50 and the image pickup device 120 may be adjusted by the manipulator.

In conclusion, in the measurement system according to the exemplary embodiments, the relative angle between the object and the image pickup device calculated according to the images of the object respectively corresponding to the at least three values of the relative angle, and the angle adjustment module adjusts the relative angle to a measurement angle according to the calculated relative angle, so as to pick up and measure the image of the object under the measurement angle. As a result, the measurement system may accurately measure the object without affected by an production error or irregular structure of the object. Therefore, the measurement system may achieve accurate automatic measurement, which facilitates mass production and increases the application of automatic detection. Moreover, the measurement system 100 may be comprised in the quality control system to prevent the measurement errors and long operation time due to people.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A measurement system configured to measure an object, the measurement system comprising:
    an illumination module configured to illuminate the object;
    an image pickup device configured to pick up an image of the object;
    an angle adjustment module configured to adjust a relative angle between the object and the image pickup device; and
    a control unit electrically connected to the image pickup device and the angle adjustment module and configured to receive an image signal from the image pickup device, the control unit being configured to command the angle adjustment module to sequentially adjust the relative angle to at least three different angles including an initial relative angle respectively having different unknown angle values, the image pickup device being configured to pick up images of the object respectively corresponding to the at least three different angles respectively having different unknown angle values, the control unit being configured to calculate the relative angle according to the images of the object respectively corresponding to the at least three different angles respectively having different unknown angle values and command the angle adjustment module to adjust the relative angle to a measurement angle according to the calculated relative angle, so as to pick up and measure the image of the object under the measurement angle,
    wherein a length of the object is automatically measured by the measurement system when the initial relative angle is adjusted to be zero based on calculating the initial relative angle using the corresponding images of the object corresponding to the at least three different angles respectively having different unknown angle values.

2. The measurement system according to claim 1, wherein under the measurement angle, an optical axis of the image pickup device is substantially perpendicular to a measured surface of the object.

3. The measurement system according to claim 1, wherein under the measurement angle, an optical axis of the image pickup device is substantially parallel to a processed surface of the object.

4. The measurement system according to claim 1, wherein the relative angle is an angle rotating around a single axis or comprises two angle components respectively rotating around two different axes.

5. The measurement system according to claim 1, wherein the angle adjustment module comprises at least one actuator supporting back-and-forth motion.

6. The measurement system according to claim 1, wherein the illumination module is configured to provide a plane light source emitting a parallel light or a diffusive light to the object.

7. The measurement system according to claim 1, wherein the control unit comprises:
    an image signal capturing device configured to receive the image signal from the image pickup device;
    a computing device configured to perform an algorithm to calculate the relative angle; and
    a command signal output device configured to output a command signal to the angle adjustment module so as to adjust the angle adjustment module according to the calculated relative angle.

8. The measurement system according to claim 1 further comprising a carrier configured to carrying the object, wherein the angle adjustment module is connected to the carrier and configured to rotate the carrier.

9. The measurement system according to claim 1, wherein the angle adjustment module is a manipulator configured to fix the object and adjust an orientation of the object.

10. The measurement system according to claim 1, wherein the angle adjustment module is a manipulator configured to fix the image pickup device and the illumination module and adjust an orientation of the image pickup device and the illumination module.

11. The measurement system according to claim 1, wherein the relative angle is an angle between the normal of a measured surface of the object and an optical axis of the image pickup device.

12. The measurement system according to claim 1, wherein the relative angle is an angle between a processed surface of the object and an optical axis of the image pickup device.

13. The measurement system according to claim 1, wherein the object is disposed between the illumination module and the image pickup device, and the object, the illumination module and the image pickup device are arranged on a straight line.

\* \* \* \* \*